(12) United States Patent
Mary et al.

(10) Patent No.: US 9,423,330 B2
(45) Date of Patent: Aug. 23, 2016

(54) METHOD OF DETERMINING THE NON-PROPAGATION THRESHOLD OF FATIGUE CRACKS AT HIGH FREQUENCY

(71) Applicants: SNECMA, Paris (FR); TURBOMECA, Bordes (FR); CENTRE NATIONAL DE LA RECHERCHE SCIENTIFIQUE, Paris (FR); ECOLE NORMALE SUPERIEURE DE CACHAN, Cachan (FR)

(72) Inventors: Caroline Mary, Paris (FR); Christophe Cluzel, Ballainvilliers (FR); Raul Fernando De Moura Pinho, Paris (FR); Arnaud Longuet, Longjumeau (FR); Sylvie Pommier, Antony (FR); Francois Vogel, Ousse (FR)

(73) Assignees: SNECMA, Paris (FR); TURBOMECA, Bordes (FR); CENTRE NATIONAL DE LA RECHERCHE SCIENTIFIQUE, Paris (FR); ECOLE NORMALE SUPERIEURE DE CACHAN, Cachan (FR)

( * ) Notice: Subject to any disclaimer, the term of this patent is extended or adjusted under 35 U.S.C. 154(b) by 0 days.

(21) Appl. No.: 14/425,999
(22) PCT Filed: Aug. 30, 2013
(86) PCT No.: PCT/FR2013/052002
§ 371 (c)(1),
(2) Date: Mar. 4, 2015
(87) PCT Pub. No.: WO2014/037654
PCT Pub. Date: Mar. 13, 2014

(65) Prior Publication Data
US 2015/0219539 A1 Aug. 6, 2015

(30) Foreign Application Priority Data
Sep. 4, 2012 (FR) .................................. 12 58250

(51) Int. Cl.
*G01N 19/08* (2006.01)
*G01N 3/32* (2006.01)
(Continued)

(52) U.S. Cl.
CPC .............. *G01N 3/32* (2013.01); *G01M 5/0016* (2013.01); *G01M 5/0033* (2013.01);
(Continued)

(58) Field of Classification Search
CPC ............. G01N 2203/0064; G01N 2203/0066; G01N 2203/0016; G01N 2203/0062; G01N 2203/0218; G01N 2203/027; G01N 2203/0282; G01N 3/08; G01N 3/32
USPC ......... 73/788, 796–799, 806, 808, 810, 813, 73/816, 826, 834, 835, 856
See application file for complete search history.

(56) References Cited

U.S. PATENT DOCUMENTS 2,154,280 A * 4/1939 Nadai ...................... G01N 3/18
374/49
(Continued)

OTHER PUBLICATIONS

Yan, Xiangqiao. "A numerical analysis of cracks emanating from an elliptical hole in a 2-D elasticity plate". European Journal of Mechanics—A/Solids, vol. 25, Issue 1, Jan.-Feb. 2006, pp. 142-153. Accessed Online <http://www.sciencedirect.com/science/article/pii/S099775380500077X>.*

(Continued)

*Primary Examiner* — Lisa Caputo
*Assistant Examiner* — Jonathan Dunlap
(74) *Attorney, Agent, or Firm* — Oblon, McClelland, Maier & Neustadt, L.L.P

(57) ABSTRACT

A method of determining the non-propagation threshold of fatigue cracks at high frequency, wherein cyclic loading is exerted on at least one testpiece having an elliptical hole in a testpiece zone, the elliptical hole having a notch at one end and the testpiece being held between two rigid masses with two rigid pre-stress plates being arranged on either side of the at least one testpiece and each fastened at its two ends to the two rigid masses, which cyclic loading is at a frequency that is selected as being equal to the resonant frequency of the assembly including the testpiece, the masses, and the stress plates, so as to generate a fatigue crack from the notch, and then once it has been observed that the crack has stopped propagating, the final length of the crack is measured and a chart is used to determine the non-propagation threshold.

10 Claims, 2 Drawing Sheets

(51) Int. Cl.
*G01N 29/04* (2006.01)
*G01N 3/38* (2006.01)
*G01M 5/00* (2006.01)
*G01M 7/02* (2006.01)

(52) U.S. Cl.
CPC ........ *G01M 5/0066* (2013.01); *G01M 5/0075* (2013.01); *G01M 7/027* (2013.01); *G01N 3/38* (2013.01); *G01N 29/043* (2013.01); *G01N 2203/0005* (2013.01); *G01N 2203/0066* (2013.01); *G01N 2203/0073* (2013.01); *G01N 2203/027* (2013.01); *G01N 2291/0258* (2013.01); *G01N 2291/2693* (2013.01)

(56) References Cited

U.S. PATENT DOCUMENTS

| | | | | | |
|---|---|---|---|---|---|
| 2,280,966 | A * | 4/1942 | Nadai | G01N 3/08 | 73/791 |
| 2,763,149 | A * | 9/1956 | Long | G01N 3/10 | 374/49 |
| 3,442,120 | A * | 5/1969 | Anderson | G01N 3/36 | 73/577 |
| 4,590,804 | A * | 5/1986 | Brull | G01L 1/06 | 73/762 |
| 4,603,588 | A * | 8/1986 | Niermann | G01N 3/22 | 73/794 |
| 4,748,854 | A * | 6/1988 | Rao | G01N 3/32 | 73/799 |
| 4,756,194 | A * | 7/1988 | Grandpierre | G01N 27/20 | 73/799 |
| 4,836,029 | A * | 6/1989 | Skala | G01N 3/24 | 73/799 |
| 5,297,441 | A * | 3/1994 | Smith | G01N 3/04 | 73/818 |
| 5,431,062 | A * | 7/1995 | Baratta | G01N 3/04 | 73/856 |
| 5,528,942 | A * | 6/1996 | Baratta | G01N 3/02 | 73/818 |
| 5,531,123 | A * | 7/1996 | Henkel | G01N 3/062 | 73/762 |
| 5,789,680 | A * | 8/1998 | Fujimoto | G01N 3/32 | 73/786 |
| 5,945,607 | A * | 8/1999 | Peppel | G01N 3/04 | 73/831 |
| 6,718,833 | B2 * | 4/2004 | Xie | G01N 3/32 | 73/789 |
| 7,568,397 | B2 * | 8/2009 | Merendino, Sr. | G01N 3/04 | 73/818 |
| 8,109,150 | B2 * | 2/2012 | Sato | G01N 3/00 | 702/181 |
| 2002/0017144 | A1 * | 2/2002 | Miles | G01N 3/32 | 73/808 |
| 2002/0162400 | A1 * | 11/2002 | Xie | G01N 3/32 | 73/812 |
| 2010/0116062 | A1 * | 5/2010 | Sato | G01N 3/00 | 73/799 |

OTHER PUBLICATIONS

Yan et al. "A numberical analysis of cracks emanating from a surface elliptical hole in infinite body in tension". Meccanica, vol. 46, Issue 2, Apr. 2011, pp. 263-278. Accessed Online <http://link.springer.com/article/10.1007%2Fs11012-010-9302-3>.*

International Search Report Issued Oct. 31, 2013 in PCT/FR13/052002 Filed Aug. 30, 2013.

Mayer, H., "Fatigue crack growth and threshold measurements at very high frequencies", International Materials Reviews, vol. 44, No. 1, pp. 1-34, XP055067429, 1999.

Anonymous: "astm E647-11E1 Standard Test Method for Measurement of Fatigue crack Growth rates", ASTM International Standard, ASTM International, US, vol. 03.01, pp. 675-720, XP008163099, 2012.

Oakley, S. Y. et al., "Prediction of the combined high-and low-cycle fatigue performance of gas turbine blades after foreign object damage", International Journal of Fatigue, vol. 29, No. 1, pp. 69-80, XP022134550, 2007.

Emery, J. M. et al., "DDSim: A hierarchical, probabilistic, multiscale damage and durability simulation system—Part I: Methodology and Level I", Engineering Fracture Mechanics, vol. 76, No. 10, pp. 1500-1530 XP026185943, 2009.

* cited by examiner

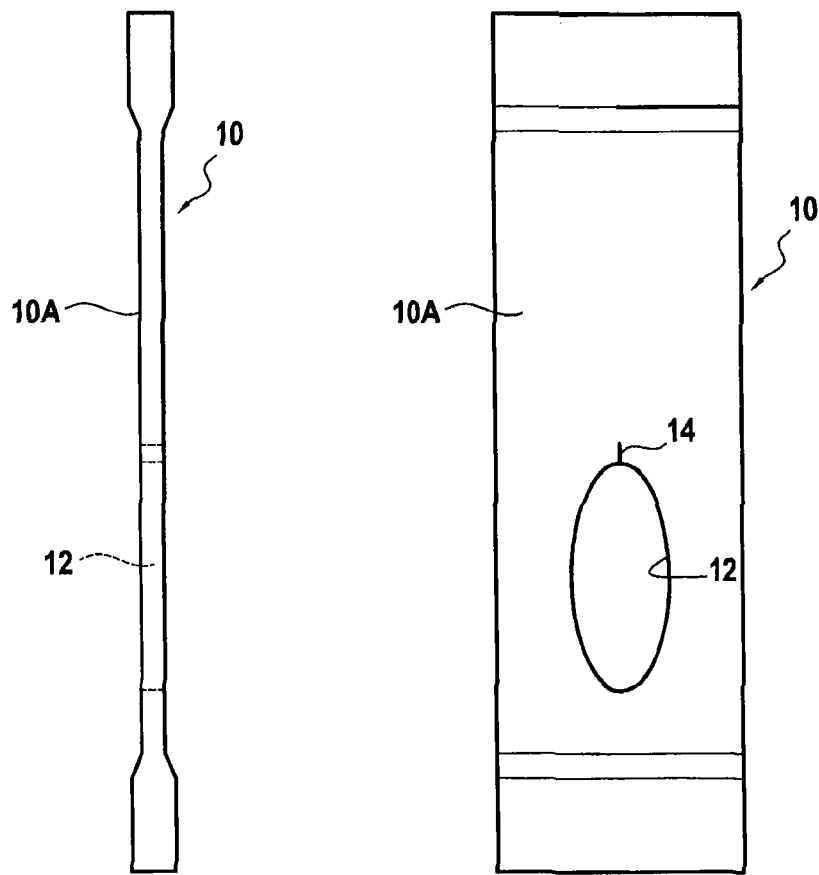
FIG.1B  FIG.1A
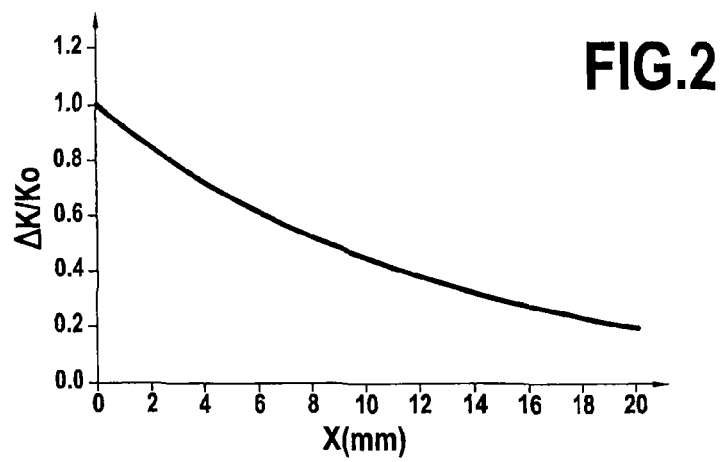
FIG.2

METHOD OF DETERMINING THE NON-PROPAGATION THRESHOLD OF FATIGUE CRACKS AT HIGH FREQUENCY

BACKGROUND OF THE INVENTION

The present invention relates to a method enabling a non-propagation threshold of fatigue cracks at high frequency to be determined for a blade of a turbine engine.

Conventionally, the sets of blades in turbojets (compressor blades and turbine blades) are stressed over a wide range of frequencies. Nevertheless, the critical frequencies are mainly those associated with the first modes in bending of the blades, which are generally situated above 500 hertz (Hz). In order to be able to dimension blades in fatigue, it is possible either to determine the dimensions of acceptable impacts on the blades, or else, more commonly, to have recourse in particular to a model for fatigue crack propagation that generally needs to be calibrated using experimental data. This data includes the threshold for non-propagation of a long crack, which threshold is written $\Delta K_{th}$ and characterizes the threshold amplitude $\Delta K$ of the stress intensity factor (SIF) beyond which a crack propagates in fatigue.

Nevertheless, for a given material, this non-propagation threshold is determined almost exclusively in quasi-static manner, which is not representative of the frequency levels to which blades are subjected during their lifetime. Furthermore, certain materials such as Ti-6Al-4V or even TiAl can be sensitive to environmental effects, which can also give rise to this threshold being dependent on frequency.

At present, the non-propagation threshold is determined by methods in which a decreasing load is applied to a testpiece using hydraulic traction machines. The force imposed is then servo-controlled to the stress intensity factor, which means that it is necessary to know how the size of the crack is varying during the test. In order to be able to do this, various instrumentation devices exist that make it possible to determine the size of the crack during testing. A first such device relies on measuring a potential difference on the basis of a current flowing through the testpiece. As the crack propagates, the resistance that is obtained as a result of this potential difference measurement increases because of the reduction in the available section in the propagation plane. The second device relies on the "compliance" method in which a strain gauge is placed on the face of the testpiece opposite from the original location of the pre-crack, and when the crack propagates for given imposed force, an increase in the measured deformation can be observed. This effect results from a decrease in the stiffness of the testpiece in traction. With a master curve giving the relationship between stiffness and crack advance, it is possible to determine the size of the crack. A third device relies on the "comb" method in which numerous strain gauges are arranged so as to form a "comb" along the cracking path. When the crack reaches a strain gauge, the strain gauge breaks. Knowing the number of strain gauges that have been broken, it is possible to determine the size of the crack. Finally, still other devices rely on the correlation between images or optical measurements from which the position of the tip of the crack is estimated with the help of a telecentric system.

All of those conventional methods rely on using a device for determining the size of the crack during testing, thus making it possible in real time to adjust the stress intensity factor (SIF) that is applied to the edge of the crack (SIF=b*S*$\sqrt{(\pi*a)}$ where b is the form factor of the crack, S is the applied stress, and a is the characteristic dimension of the crack). A decrease in the SIF is thus applied and the threshold is considered as being reached as soon as the speed of advance of the crack (as measured during the test) becomes less than a given value, e.g. $10^{-10}$ meters per cycle (m/cycle), as proposed in the ASTM E647 standard.

Apart from the fact that the threshold is always characterized under quasi-static conditions (1 Hz to 30 Hz), and therefore on the assumption that the non-propagation value that is obtained is constant as a function of frequency, which is not true, the major drawback of those conventional methods is that they require the size of the crack to be determined in situ. Devices for measuring potential can be applied only to a material that is conductive and they require a data acquisition and processing system that is fast in order to be able to perform regulation. As a general rule, this is not possible at high frequencies such as those to which parts are subjected in operation and for which it is desired to characterize the materials of which they are made (>500 Hz). The compliance method can be applied to any homogeneous material, but it likewise requires a fast data acquisition and processing system in order to perform regulation, which is likewise incompatible with the frequencies at which it is desired to perform measurements. The comb method does not necessarily lead to effective servo-control. The length of the crack can be determined in discrete manner only, i.e. at the locations where the strain gauges are positioned. It can then happen that overloading effects occur at the tip of the crack. Finally, optical measurements can be used only when the propagation speed of the crack is sufficiently slow. Between two measurements, the variation in the length of the crack must be small in order to avoid the effect of overloading the tip of the crack.

OBJECT AND SUMMARY OF THE INVENTION

The present invention thus has the object of mitigating the above-mentioned drawbacks by proposing a method of determining the non-propagation threshold of fatigue cracks at high frequency (>500 Hz) in a structural testpiece having a particular shape that makes such determination possible.

To this end, the invention provides a method of determining the non-propagation threshold for fatigue cracks at high frequency, wherein cyclic loading is exerted on at least one testpiece having an elliptical hole in a test zone, the elliptical hole having a notch at one end and the testpiece being held between two rigid masses with two rigid pre-stress plates being arranged on either side of said at least one testpiece and each fastened at its two ends to said rigid masses, which cyclic loading is at a frequency that is selected as being equal to the resonant frequency of the assembly comprising the testpiece, the masses, and the stress plates, so as to generate a fatigue crack from said notch, and then once it has been observed that the crack has stopped propagating, the final length of the crack is measured and a chart is used to determine said threshold $\Delta K_{th}$ for non-propagation of the crack by fatigue, said cyclic loading being obtained by an electrodynamic vibrator pot securely fastened with the help of rigid uprights to a structure supporting said two rigid masses and including a thrust rod for transmitting said cyclic loading to said assembly comprising the testpiece, the masses, and the stress plates.

With this method, there is no longer any need to measure the length of the crack while testing is taking place, nor is there any need to perform servo-control on the basis of such a measurement.

Preferably, said stopping of the crack is observed by counting a predetermined number of loading cycles (typically lying in the range 8 million to 12 million cycles).

The invention also provides a test device enabling the non-propagation threshold for fatigue cracks at high frequency to be determined, the device comprising:
- at least one testpiece having an elliptical hole in a test zone, the hole having a notch at one end;
- two rigid masses between which said at least one testpiece is held;
- two rigid pre-stress plates arranged on either side of said at least one testpiece and each fastened at its two ends to said two rigid masses; and
- an electrodynamic vibrator pot securely fastened by means of rigid uprights to a structure supporting said two rigid masses and including a thrust rod for transmitting cyclic loading to said at least one testpiece via said two rigid masses, said cyclic loading having a frequency that is selected to be equal to the resonant frequency of the device so as to generate a fatigue crack from said notch, the length of the fatigue crack, once it has been observed that the propagation of the crack has stopped, determining said non-propagation threshold $\Delta K_{th}$ for fatigue cracks.

Thus, by exciting the setup in dynamic traction at its resonant frequency with the help of an electrodynamic vibrator pot it is possible to achieve loading levels that are high enough to generate a fatigue crack, and the stopping of the propagation of that crack enables the non-propagation threshold to be determined.

Preferably, the device further includes one or more additional masses for varying said loading frequency by modifying said resonant frequency.

Advantageously, said notch is made at one end of the major axis of said elliptical hole and in the direction of said loading.

Preferably, said uprights are rigid brackets.

Advantageously, said testpiece is initially put into compression by traction on said two pre-stress plates obtained by progressively reducing clearance that exists initially between one of said ends of said two pre-stress plates and a facing one of said two rigid masses.

According to the invention, said resonant frequency of the device lies in the range 300 Hz to 2000 Hz.

BRIEF DESCRIPTION OF THE DRAWINGS

Other characteristics and advantages of the present invention appear from the following description made with reference to the accompanying drawings, which show an implementation having no limiting character, and in which:

FIGS. 1A and 1B show a testpiece used in a test device enabling the non-propagation threshold for fatigue cracks to be determined in accordance with the invention;

FIG. 2 shows the decay rate of $\Delta K$ for the testpiece of FIGS. 1A and 1B;

DETAILED DESCRIPTION OF THE INVENTION

Figure 3:
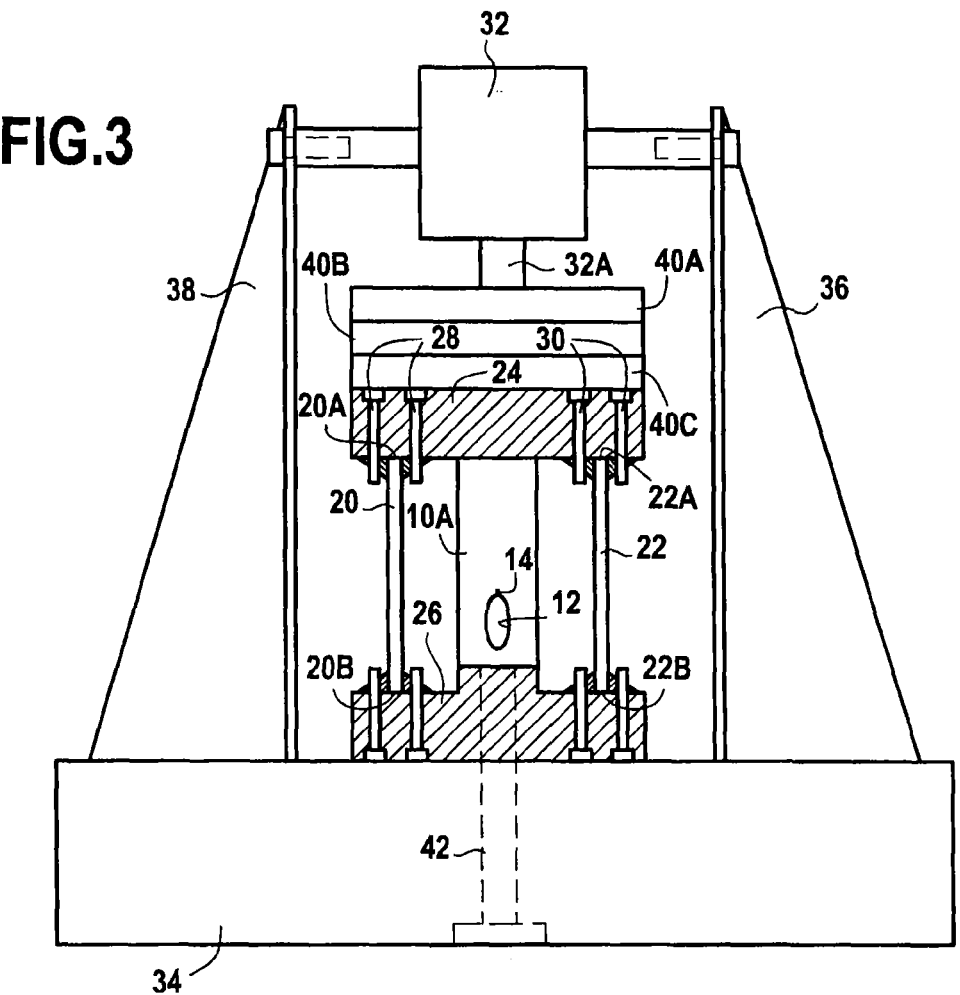
FIG. 3 shows the test device for use in determining the non-propagation threshold for fatigue cracks in accordance with the invention.

The invention proposes applying an external cyclic load of constant mean and amplitude on a structural testpiece that includes an elliptical hole that has been pre-notched at the edge of the hole. The presence of this elliptical hole generates a stress gradient, and its ellipticity ratio associated with the size of its semi-major axis then makes it possible to ensure that the stress intensity factor at the tip of the crack presents the desired decay rate for determining the non-propagation threshold for fatigue cracks. The crack then stops on its own under this decaying load, and it suffices to measure the final length of the crack after it has stopped in order to be able to determine the value of $\Delta K_{th}$. The length of the crack is measured after the test has terminated, with scaling of the test merely requiring the use of a chart.

FIGS. 1A and 1B show the shape of the testpiece needed for use in the test device of the invention. The testpiece 10 is preferably rectangular in shape and has an elliptical hole 12 in its central test portion 10A, which hole generates a stress gradient in the testpiece. At one end of the hole, and more particularly at the end of its major axis, and in the stressing (loading) direction, the testpiece has a notch 14, e.g. made by electoerosion (an electrical discharge machined (EDM) notch with a straight front), so as to make it easy to initiate a fatigue crack. As shown, the testpiece preferably has reduced thickness in the test zone 10A.

When the testpiece is subjected to compression loading, traction stresses appear at the edge of the hole, because of the elastic Poisson effect. With cyclical loading in compression (or traction-compression), the crack opens and closes on each cycle and therefore propagates by fatigue. In the absence of a crack, stress at the edge of the hole is positive, it decreases progressively in the stress concentration zone, and it tends to zero on going away from the hole. Consequently, if a crack propagates away from the edge of the hole, its stress intensity factor (SIF) decreases with increasing propagation length of the crack. The fatigue crack stops when the amplitude of the stress intensity factor reaches the non-propagation threshold $\Delta K_{th}$ during the propagation stage.

The shape of the elliptical hole determines the decay rate of the stress intensity factor with advance of the crack. It is therefore important to dimension the elliptical hole (major axis and ratio of minor axis over major axis) so as to obtain the desired curve for $\Delta K$ as a function of crack length. The decay rate of $\Delta K$ decreases with increasing ratio of the minor axis over the major axes, and with decreasing size of the minor axis. An optimum decay rate serves both to avoid overloading effects at the tip of the crack and to reduce uncertainty in measuring the length of the crack (and thus in calculating $\Delta K_{th}$) once the crack has stopped propagating.

FIG. 2 shows this decay rate that, in accordance with the above-specified standard, is expressed using the following formula:

$$\Delta K(x)/\Delta Ko = \exp(-0.08x)$$

where x is the distance between the tip of the crack and the edge of the elliptical hole (in millimeters (mm)) and $\Delta Ko$ is the maximum amplitude reached by $\Delta K$ close to the elliptical hole.

When dimensioning the testpiece, care should therefore be taken to ensure that the variation in $\Delta K$ with advance of the crack generated by the elliptical hole 12 and the notch 14 makes it possible to cover the expected threshold. It is the shape of the testpiece that determines how the stress intensity factor varies with crack advance. For example, for a rectangular testpiece having a test zone 10A with dimensions of 70×30×3 (length, width, and thickness in millimeters), an ellipse having a major axis of 24 mm and a minor axis of 12 mm is positioned with its center 25 mm away from the bottom boundary of the test zone. The notch is made over 1.5 mm from the top of the major axis of the ellipse, and along the major axis.

The test device for determining the non-propagation threshold for fatigue cracks at high frequency is shown in FIG. 3. The testpiece 10 is subjected to static pre-loading by two rigid pre-stress plates 20 and 22 (e.g. made of composite material) that are arranged on either side of the testpiece and that are fastened at one of their ends 20A, 22A to one of two rigid masses 24, 26 between which the testpiece is engaged, with the other ends 20B, 22B of these two plates being fastened with initial clearance to the other one of these two masses 22. This initial clearance may be introduced with the top rigid mass 24 or with the bottom rigid mass 26, but advantageously the progressive reduction of this initial clearance is achieved via the attachment with the top rigid mass by a pair of fastener screws 28, 30 that, by acting in traction on the two pre-stress plates, then make it possible to apply compression to the testpiece. The masses 24, 26 serve to add stiffness and to modify the resonant frequency of the assembly comprising the testpiece and the pre-stress plates.

The setup as obtained in this way is subjected to vibration by means of an electrodynamic vibrator pot 32 that is rigidly fastened to the structure of the device, e.g. a support slab 34, and that transmits the force delivered by the vibrator pot to the setup comprising the rigid pre-stress plates and masses surrounding the testpiece via one or more additional masses 40A-40C. In order to obtain a maximum amount of deformation on each traction cycle applied to the testpiece, the loading frequency is taken to be equal to the resonant frequency in traction of the setup. Since this frequency is equal to the square root of the stiffness of the system (comprising the testpiece+the pre-stress plates) divided by the moving mass, adding or removing additional masses 40A-40C serves to vary this resonant frequency and thus to perform tests for measuring the crack non-propagation threshold $\Delta K_{th}$ at different frequencies, at high frequencies preferably lying in the range 300 Hz to 2000 Hz. Since the modal amplification is large, even for a relatively small imposed force, the deformation of the testpiece can be large, as can the stress intensity factor applied at the tip of the crack.

Crack propagation coming to a stop is observed merely by counting the number of cycles applied, which number lies preferably in the range 8 million to 12 million cycles. This value is selected from an estimated order of magnitude for the threshold $\Delta K_{th}$ and from the propagation speed. The cyclic stressing can thus itself be stopped and the testpiece can be removed from the device in order to measure the final length of the crack and then to determine said non-propagation threshold $\Delta K_{th}$ for fatigue cracks with the help of a chart.

Naturally, it is appropriate to use fastener means, e.g. of the screw type 42, to fasten the setup rigidly to the support slab 34. Any separation therefrom, even if only local, can lead to a loss in the transmission of the mechanical energy delivered by the electrodynamic vibrator pot 32 to the setup, and thus also to the testpiece 10.

Thus, by using the above-described testpieces, the following results have been obtained: for a load ratio of 0.7 corresponding to a stress amplitude on the testpiece of 80.7 megapascals (MPa) and for a stressing frequency of 803 Hz, the crack traveled 8.6 mm before stopping. Using the chart, $\Delta K_{th}$ is determined as being equal to 2.7 megapascal-root meters (MPa.$\sqrt{m}$).

Figure 4:
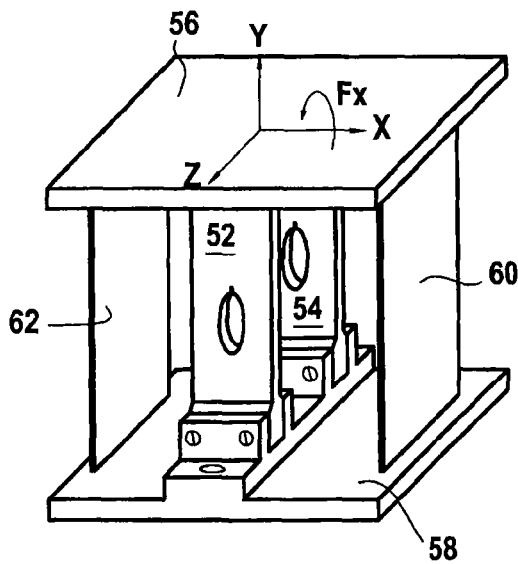
FIG. 4 shows a two-testpiece variant of a portion of the FIG. 3 device.

It should be observed that although the above description makes reference to a traction setup, it is clear that is it also possible to envisage bending type loading. In particular, as shown in FIG. 4, if the setup contains two testpieces 52, 54 instead of only one, and if the spacing between the two testpieces is sufficiently great, then even if the loading imposed by the setup comprising two masses 56 and 58 and two pre-stress plates 60, 62 is of the bending type, the stress field applied to one or the other of the testpieces can be considered as being practically in traction.

The invention claimed is:

1. A method of determining a non-propagation threshold for fatigue cracks, comprising:
    initiating a fatigue crack by cyclic loading on at least one testpiece having an elliptical hole in a test zone, the elliptical hole having a notch at an apex of the elliptical hole for initiating a fatigue crack and the testpiece being held between two rigid masses with two rigid pre-stress plates being arranged on either side of said at least one testpiece and each fastened at its two ends to said two rigid masses, which cyclic loading is obtained by an electrodynamic vibrator pot securely fastened by rigid uprights to a structure supporting said two rigid masses and including a thrust rod for transmitting said cyclic loading to an assembly comprising the at least one testpiece, the two rigid masses, and the two rigid pre-stress plates, at a frequency that is selected as being equal to the resonant frequency of said assembly, so as to generate said fatigue crack from said notch;
    determining that the fatigue crack has stopped propagating;
    measuring a final length of the fatigue crack; and
    using a chart showing a decay rate of $\Delta K_{th}$ function of crack length to determine said threshold $\Delta K_{th}$ for non-propagation of fatigue cracks.

2. The method according to claim 1, wherein said determining that the crack has stopped comprises counting a predetermined number of loading cycles.

3. The method according to claim 2, wherein said predetermined number lies from 8 million to 12 million loading cycles.

4. The method according to claim 1, wherein said cyclic loading lies at a frequency from 300 Hz to 2000 Hz.

5. The method according to claim 1, further comprising varying the cyclic loading frequency by modifying said resonant frequency.

6. The method according to claim 1, wherein said notch is made at one end of the major axis of said elliptical hole and in a direction of said loading.

7. The method according to claim 1, further comprising initially putting said at least one testpiece into compression by traction on said two pre-stress plates with progressively reducing clearance that exists initially between one of said ends of said two pre-stress plates and a facing one of said two rigid masses.

8. The method according to claim 1, wherein said uprights are rigid brackets.

9. The method according to claim 1, wherein the decay rate is expressed as $\Delta K(x)/\Delta K_o = \exp(-0.08x)$, in which x is a distance between a tip of the crack and an edge of the elliptical hole in millimeters, and $\Delta K_o$ is a maximum amplitude reached by $\Delta K$ close to the elliptical hole.

10. A method of determining a non-propagation threshold for fatigue cracks, comprising:
    generating at least one testpiece having an elliptical hole in a test zone, the elliptical hole having a notch made at an apex in a direction of a cyclic loading;

initiating a fatigue crack from said notch by said cyclic loading at a predetermined frequency on said at least one testpiece;
when the fatigue crack has stopped propagating, stopping the cyclic loading;
measuring a final length of the fatigue crack; and
using a chart showing a decay rate of $\Delta K_{th}$ function of crack length to determine a threshold $\Delta K_{th}$ for non-propagation of fatigue cracks.

\* \* \* \* \*